Figure 1:
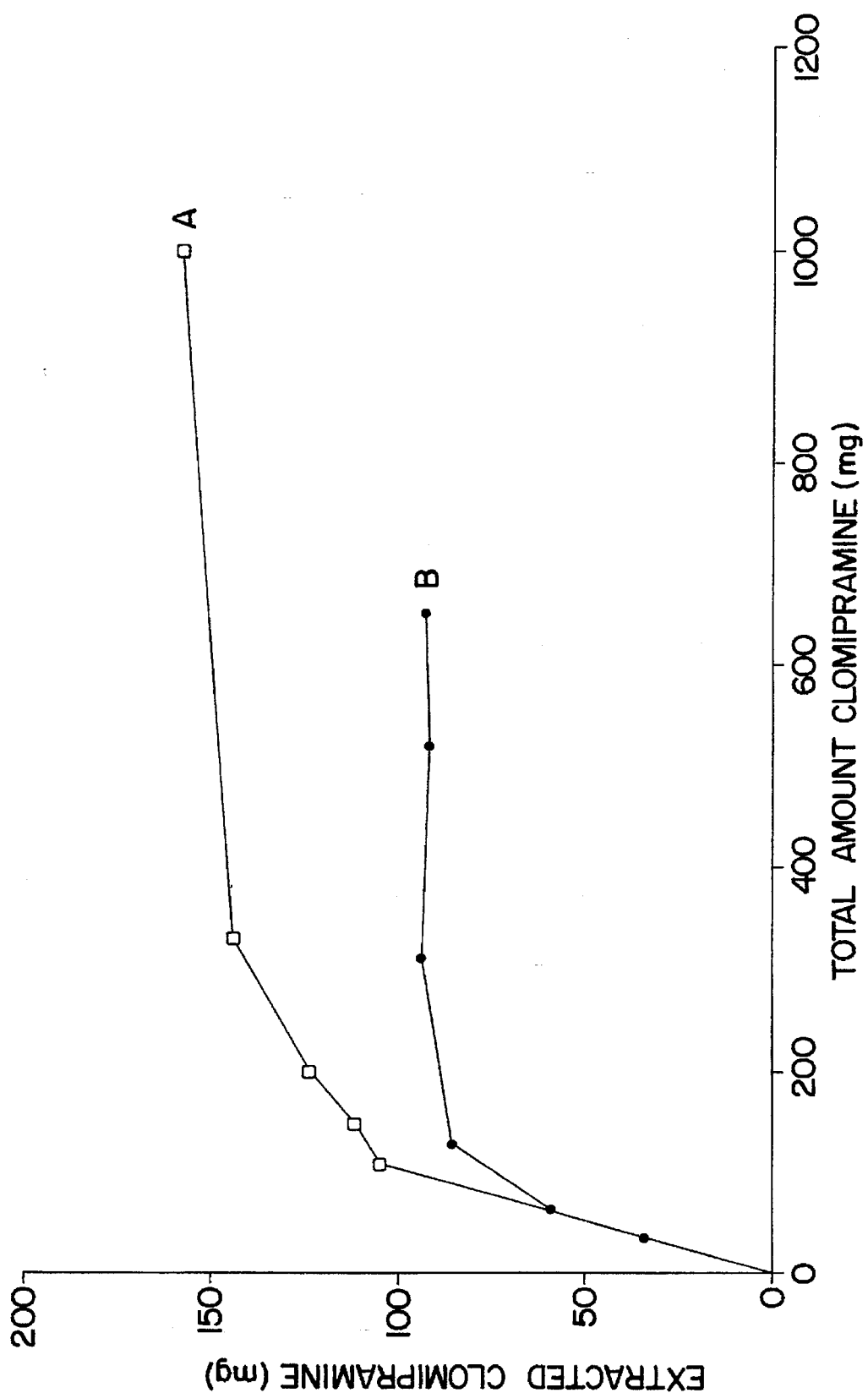

United States Patent [19]

Bergwitz-Larsen et al.

[11] Patent Number: 5,643,560

[45] Date of Patent: Jul. 1, 1997

[54] DRUG FORMULATION WITH ION-EXCHANGERS

[75] Inventors: Carl-Aage Bergwitz-Larsen, deceased, late of Stockholm, by Emma K. Bergwitz-Larsen, legal representative; Bertil Hillgren Ulf, Storvreta; Anders Ragnarsson Gert, Bro, all of Sweden

[73] Assignee: Pharmacia & Upjohn AB, Stockholm, Sweden

[21] Appl. No.: 211,863

[22] PCT Filed: Oct. 16, 1992

[86] PCT No.: PCT/SE92/00724

§ 371 Date: Jun. 21, 1994

§ 102(e) Date: Jun. 21, 1994

[87] PCT Pub. No.: WO93/07860

PCT Pub. Date: Apr. 29, 1993

[30] Foreign Application Priority Data

Oct. 24, 1991 [SE] Sweden ................... 9103110

[51] Int. Cl.⁶ ........................... A61K 47/32; A61K 47/36
[52] U.S. Cl. ........................... 424/78.12; 424/78.11
[58] Field of Search ................... 424/78.1, 78.12, 424/78.11

[56] References Cited

U.S. PATENT DOCUMENTS

| | | | |
|---|---|---|---|
| 2,697,059 | 12/1954 | Gustus | 424/78.1 |
| 2,990,332 | 6/1961 | Keating | 167/65 |
| 4,221,778 | 9/1980 | Raghunathan | 424/31 |
| 5,071,646 | 12/1991 | Malkowska et al. | 424/78.12 |

FOREIGN PATENT DOCUMENTS

| | | | |
|---|---|---|---|
| 0 331 471 A1 | 9/1989 | European Pat. Off. . | |
| 0 367 746 A2 | 5/1990 | European Pat. Off. . | |
| 0 367 746 A3 | 5/1990 | European Pat. Off. . | |
| 925890 | 5/1963 | United Kingdom | 424/78.1 |
| 1218102 | 3/1968 | United Kingdom . | |
| 1 218 192 | 1/1971 | United Kingdom . | |
| 1358001 | 6/1974 | United Kingdom . | |

OTHER PUBLICATIONS

Montgomery, S.A., et al., The Risk of Suicide with Antidepressants, St. Mary's Hospital Medical School, London, England, (1988) pp. 15–24.

*Primary Examiner*—Peter F. Kulkosky
*Attorney, Agent, or Firm*—Pollock, Vande Sande & Priddy

[57] ABSTRACT

The invention relates to the use of, and methods to obtain, ion exchanger complexes with psychotropic drugs for reducing toxic side effects and lethality when overdosing the drug. The invention includes methods and compositions for modifying the total amount of drug released from the complex in the gastro-intestinal tract by adding a substance which affects the ion exchange process. The additional substance may be a salt which generates an ion with higher or similar affinity to the ion exchanger when compared to the drug. The additional substance may be a counter ion in an additional complex with an ion exchanger.

8 Claims, 1 Drawing Sheet

DRUG FORMULATION WITH ION-EXCHANGERS

FIELD OF INVENTION

The present invention relates to a the use of ion exchange complexes in medicine to avoid or substantially reduce toxicity and lethality if overdosing psychotropic drugs as well as a method for manufacturing of pharmaceutical preparations thereof including methods to adjust the preparations to suit drugs with different therapeutic dose levels.

BACKGROUND OF THE INVENTION

Psychotropic drugs represents a special safety problem as the patients due to their psychological disorders are more prone to accidental or deliberate overdosing than other groups of patients. Most of the drugs used in the treatment of severe depressions are for example potentially lethal in doses that are available to patients with a high risk of suicide.

Table 1, obtained from the data system SWEDIS covering the Swedish market, may serve as an example to illustrate that deaths from overdosage of psychotropic drugs are a common problem.

The risk of suicide with antidepressants have, for example, been discussed in detail by Montgomery et al. (S. A. Montgomery, M. T. Lambert and S. P. J. Lynch, The Risk of Suicide with Antidepressants, International clinical psychopharmacology, Suppl. 2, 15–24, 1988) including mortality rates and problems associated with treatment of patients who have episodes of deliberate self-harm due to depression or personality disorders. Psychotropic agents can be divided in different groups such as antidepressants, antipsychotic agents, anxiolytic agents and, hypnotic and sedative agents. Significant toxic effects of antidepressant agents of the tricyclic or tetracyclic type such as clomipramine, imipramine, amipramine, desipramine, nortriptyline, dothiepin or maprotline are, for example, relatively common and estimates of prevalence have run as high as 5% (adapted from Goodman and Gilman's The Pharmacological Basis of Therapeutics, Seventh Edition, Macmillan Publishing Comp., New York, 1985). Clinical consequences of the antimuscarin effects are e.g. dry mouth, epigastrial distress, constipation, dizziness, tachycardia, palpitation, blurred vision and urinary retention. In addition tricyclic antidepressive agents may give rise to manic reactions and cases of confusion and delirium are common especially among elderly patients.

Acute poisoning with tricyclic and tetracyclic antidepressants is common and often life threatening. Patients suffering from severe depression have a high risk of suicide and have often access to potentially lethal doses of antidepressants. The risk can be reduced to some extent by not dispensing more than e.g. a weeks supply of an antidepressant to an acutely depressed patient. It is well known from medical praxis that it will in general take 2–3 weeks before substantial improvements are obtained. The symptoms may even be aggravated during the first phase of the treatment. This initial part of the treatment will consequently be a large problem regarding the safety of the patient.

The antipsychotic drugs have in general a high therapeutic index and are considered as relatively safe agents. Occasional deaths from overdosage have been reported however, especially when the drugs have been ingested concurrently with alcohol or other drugs. Antipsychotic or neuroleptic drugs potentiate e.g. the action of other central-nervous system depressants and extreme care has therefore been recommended if a need arises to use them concurrently with alcohol, hypnotics such as barbiturates, narcotic analgetics or general anesthetics.

The benzodiazepines, from the group hypnotic agents and sedatives and the group of anxiolytic agents, are considered as relatively safe drugs but overdosage is sometimes fatal. Alcohol is a common contributor to deaths involving benzodiazepines. The safety risks are consequently not restricted to antidepressants but should be considered also for other groups of psychotropic agents.

Tricyclic and tetracyclic antidepressants represents, from a chemical point of view, a rather well characterized group including in general cyclic structures and a substituted chain including at least one aminogroup. Amines are basic substances that can form complexes with cationic exchangers. Substances that includes ionizable groups such as amines, aromatic alcohols and carboxylic acids can form complexes with anionic or cationic ion exchangers, below refered to as ion exchange resins.

PRIOR ART

Ion exchange materials are used to exchange ions between a solution and an insoluble solid. Ion exchange resins may be of both inorganic and organic origin. The ion exchange which occurs between the complex alumino-silicates, the zeolites, and raw water is, for example, used for softening water. Zeolites in the form of its sodium salt treated with tap water containing calcium ions gives an exchange of ions and calcium is taken up by the insoluble solid zeolite while a corresponding amount of sodium ions goes into solution.

Organic ion exchangers consist of hydrocarbon polymers in which ionizable exchange groups have been introduced i.e. fixed anionic (cationic exchangers) or cationic groups (anionic exchangers) which have mobile cations and anions, respectively, associated with them. Organic ion exchange resins are much more stable than the zeolites at extreme pH values and can be prepared to have highly polar groups in their structure giving a high exchange capacity and are thus of interest in the pharmaceutical field.

Many resins are styrene-divinyl-benzene polymers in which styrene gives linear polymer chains and the divinyl-benzene crosslinks the chains. The proportion of divinyl-benzene in the mixture which is polymerized determines the porosity and the physical properties of the resin. A high divinyl-benzene content gives a hard resin of low porosity, whereas a low proportion produces a soft gel-like polymer which swells easily in contact with water and is highly porous. These different properties have been important in pharmaceutical applications of ion exchange resins.

Drug-ion exchange complexes have for example been used in order to obtain quickly dissolving preparations of sparingly soluble drugs (see GB 1358001) or to protect the oesophagus from tissue irritating drugs such as emepronium, doxycycline and propanolol while keeping a good biological availability, as described in EP 91403. This reference cites complexes between carrageenans, a natural sulphated polysaccharide, which can be used as an ion exchanger, and certain drugs. Another approach has been to use ion exchange complexes in controlled release preparations by using complexes that are able to form a matrix giving a sustained release of the drug by a slow diffusion of drug and counterions during the release process. The release rate is affected by the particle size and the degree of cross-linking of the resins. By choosing appropriate ion exchangers it is consequently possible to affect the biopharmaceutical properties i.e. to get a rapid or a prolonged release of the drug. Various such applications are exemplified in the following patent documents GB 1176194, GB 1218102, U.S. Pat. No. 4,221,778, EP 139881 and in EP 367746.

It has now, as described in the present invention, surprisingly been found that complexes between ion exchange materials and psychotropic agents can be designed and used to eliminate or substantially reduce toxic effects at overdosage of psychotropic agents which should represent a substantial improvement in the treatment of patients that due to psycological disorders are prone to accidential or deliberate overdosing of prescribed drugs. The invention should represent a special advantage in the treatment of patients that due to severe depression have a high risk of suicide.

FIG. 1.

Extraction of clomipramine from clomipramine carrageenan complex in presence of a carrageenan complex of a counter-ion of less affinity to the complex binder by 1 1 solution simulating gastric environment.

A=Clomipramine carrageenan complex according to example 5.

B=Clomipramine carrageenan complex according to example 5 and a competing complex according to example 3.

DETAILED DESCRIPTION OF THE INVENTION present invention relates to a method for reducing the toxic side-effects and lethality when overdosing psychotropic drugs by means of using ion exchangers. The invention also provides compositions of a psychotropic agent complexed to an ion exchanger, which have reduced toxic side-effects and lethality at overdosage.

More particulary the invention relates to compositions and methods where a drug-ion exchanger complex is mixed with an additive which modifies the release of the drug. These additives are additional substances, which will affect the amount of available ions for ion exchange in the gastrointestinal area and comprise ionizable salts, protolytes or additional complexes of ion exchangers and counter ions.

Another aspect of the invention is the use of an ion exchanger for reducing the toxic side-effects and lethality when overdosing a psychotropic drug.

A further aspect of the invention is the use of a complex of a drug and an ion exchanger for the preparation of a medicament that reduces the toxic side-effects and lethality when overdosing the drug.

The present invention also provides ion exchange complexes with psychotropic drugs. The complexes which are stable and physically and chemically well defined entities represent an improvement over established preparations as described below.

Psychotropic agents i.e antipsychotic agents, anxiolytic agents, hypnotic and sedative agents and antidepressants with ionizable groups such as amines, aromatic alcohols, and carboxylic acids can be bound to anionic and cationic ion exchange materials. Typical such examples are tricyclic antidepressants with ionizable aminogroups. This group of psychotropic agents includes drugs such as clomipramine, imipramine, amitriptyline, desipramine and nortriptyline which can be bound to cationic ion exchange materials as illustrated in example 1–5 and 7–8. In all these examples, less than 5% of the drug could be extracted in distilled water while all drug was released in liquids containing excessive amounts of cations.

Also in other groups of psychotropic agents there are a number of drugs suitable for complex formation with ion exchangers e.g. chlorpromazine, chlorprothixene, chlordiazepoxide, propiomazine and maprotiline.

Suitable pharmaceutically acceptable ion exchange materials include co-polymers of methacrylic acid and divinylbenzene, copolymers of divinylbenzene and dimethylaminomethyl- or trimethylaminomethyl polystyrene or sulphonated polystyrene, sulphated polysaccharides such as alfa-D-glucopyranosil polymers (dextranes) and sulphated copolymers of galactose and 3,6-anhydrogalactose.

A typical example of such an material, used below to illustrate the present invention, vention, is the carrageenans which are salts of polysaccharide sulphate esters obtained from seaweed of the class Rhodophyceae and extracted to yield gelling agents in a powdered form. The carrageenan is a 3,6-anhydrogalactose and galactose copolymer existing mainly as kappa-, iota- and lambda carrageenan, differing in the degree of sulphation. The galactose units are joined by altering $\alpha$ 1–3, $\beta$ 1–4 glycoside linkages. The carrageenan is used in Pharmacy (U.S.N.F) and in the food industry (E407) and is therefore suitable for oral drug delivery systems.

Another example, also used to illustrate the invention below, is the AG 50W-X4 cationic ion exchange resin, a sulphonated polystyrene crosslinked with 4% divinylbenzene (DVB) and having a particle diameter of 75–180 µm. Numerous examples of the use of DVB crosslinked sulphonated polystyrenes in pharmaceuticals exists. The sodium form of polystyrene sulphonate is described scribed in USP. A third ion exchange material used to illustrate the invention is dextran sulphate, a polymer composed of $\alpha$-D-glucopyranosyl units with up to three sulphate groups per monomer.

One aspect of this invention is that ion exchangers and drugs can be selected to give a normal biological availability when the complex is administered in normal doses while at large amounts, corresponding to an acute overdose of drug, the amount of liquid and ions will be limiting factors and the drug release will cease. As the drug release from the sparingly soluble and biologically inert complex is practically prevented there will be little further systemic drug absorption into the general circulation. Sever toxic or lethal drug concentrations in the blood system will thus be avoided.

Another aspect of this invention is the design of preparations that increase the possibilities to obtain a protective effect towards toxic overdoses while keeping appropriate biopharmaceutical properties at normal doses.

The limiting effect of the amount of liquid and ions in the gastrointestinal tract is directly dependent on the amount of the ion exchange material and its ion binding capacity. The capacity of the ion exchangers to bind the drug (primarily by ion binding but in some cases also to a minor degree by other interactions) determines the amount of drug bound to the exchanger to a fixed level. Therefore adjustments may be needed in order to tailor the present invention to suite a specific drug. This can be done by adding ions to a final solid preparation as in example 6 and table 10. It may thus be possible to ensure that a sufficient amount of a high dosage drug is released to give therapeutic drug concentration levels.

The possibility to adjust the properties by adding ions to a solid preparation is limited as rather large amounts will be needed to have a more substantial impact on the total amount of ions in the gastro intestinal system. Addition of a competing complex to the active complex in the final preparation is a more powerful method and should enable an accurate adjustment within broad dose limits. The choice of ions to be included in the competing complex is not very critical except that the ions should have a low toxicity and be pharmaceutically acceptable. Any ion of the same type as the drug, cationic or anionic, with a less or similar ability to bind to the exchanger will compete with the drug for the available counterions present in the gastro intestinal tract thus giving the possibility to accentuate the power of the present invention in terms of preventing toxic effects at overdosage of the drug.

It should also be possible to use different ion exchange resins for the competing complex and for the active complex as long as there is a competition for the available counter ions in the gastro intestinal system. The choice of ions and the amount and type of ion exchange resin is dependent on the drug and its normal and toxic dose levels and a proper selection will thus have to be carried out in each individual case.

It is of course also possible to use other drug ions as competing ions whenever a fixed combination of two or more drugs is appropriate.

When an additional complex is added to the drug-ion exchanger complex, it is essential, however, that the additional complex should not contribute significantly to the release of the actual drug. The ions, inert or drug ions, in the additional complex should consequently have a lower, or similar, affinity to the ion exchanger than the drug which toxicity we are intending to reduce. In other cases, ions released from the additional complex may release substantial amounts of the drug by an ion exchange process. This should be the case both when the drug complex and the additional complex includes the same ion exchanger or when they include different ion exchangers.

In the selection of drugs and ion-exchangers, the stability of the complex in physiological pH-levels in the gastro intestinal tract should also be considered. Complexes between strong cationic exchangers and reasonably strong bases will e.g. be stable within the normal pH range of the gastrointestinal system. This can easily be tested in-vitro. Anion complexes will tend to dissociate at low pH values i.e. there is a risk that the drug will be released completely in the stomach also at high dose levels. This can be prevented by using enteric coatings, i.e. protective polymer coatings that are insoluble in the low pH in the stomach but is easily dissolved in the intestine. Enteric coating is a well known and established pharmaceutical technology.

Preparations and Dissolution Tests

The complexes between the drugs and the ion exchange materials are insoluble or only sparingly soluble in water. The main part of the active substance will be complex-bound and biologically inactive in the absence of ions. In the gastro-intestinal fluids, however, the active entity is released in presence of ions by ion exchange with the cations or anions to an extent depending on the amount of liquid and ions present. This is illustrated in table 2 showing the dissolution of clomipramine from 40 mg clomipramine carrageenan complex in 1000 ml of 0.15M hydrochloride acid, In this case all of the drug was released after 30 min (the measured release in this case exceeds 100% due to normal experimental errors).

There is a considerable secretion of ions and liquid in the gastro intestinal tract as can be seen in table 3. If a reasonable amount of a drug-ion exchange complex is administered by the oral route and preferably spread over a large area of the gastro-intestinal system by using disintegrating tablets, capsules or suspensions, a rapid contact with sufficient amounts of ions will ensure a complete release of the drug.

The amount of liquid and the ionic strength should however be limiting factors as illustrated in table 4 and 5. In table 4, 100 mg of complexes between carrageenan and the tricyclic antidepressants desipramine, imipramine and clomipramine, examples 4, 2 and 5 respectively, were tested in various amounts of an extraction medium consisting of a 0.15M sodium chloride solution in water. The difference in the amount of liquid needed to release all of the drug in table 4 is due to differences in the binding between the ion exchanger and the different drugs.

In table 5 the complex of clomipramine and carrageenan, described by example 5, was tested with different concentrations of sodium chloride present in a limited volume (0.15 l).

The overdosage situation is illustrated by the study presented in tables 6 and 7 where increasing amounts of complex bound drug was equilibrated with a solution of a specific volume and ionic strength.

Table 6 and 7 also shows that the type of counterion is of little importance. An ion exchange process took place both in presence of hydrogen and sodium ions, two types of ions that are present in the gastro-intestinal tract. The same situation as above is illustrated for two other ion exchangers, AG 50W-X4 and dextran sulphate, table 8 and 9, respectively.

Example 6 and table 10 illustrate a study of adding ions generated from sodium chloride to a solid preparation of clomipramine carrageenate and the amount of clomipramine extracted from the complex.

Another method to modify the amount of drug released from the complex is to add an ion exchange complex including another substance to the active drug-ion exchange complex. This method is useful in cases when a relatively small amount of drug should be released. This principle is illustrated in table 11 and FIG. 1, where the competing substance for simplicity is represented by another amine from the same therapeutic group (amitriptylin).

Examples 9–11 illustrate that the drug-ion exchanger complex can be used as in capsules or together with pharmaceutical excipients in tablets or suspensions. In the later case suitable excipients, with a low ion content, should preferably be selected to get a low content of free drug in the vehicle (e.g. less than 1% in example 11).

Comparative Toxicity Study

A comparative study between clomipramine hydrochloride and clomipramine carragenate, prepared according to example 5, was performed in mini-pigs. For ethical reasons an animal model was used and mini-pigs were considered appropriate due to similarities with men both regarding the gastro-intestinal system and some cardiovascular system characteristics.

Acute overdose with tricyclic antidepressants, such as clomipramine, in man gives well known cardiotoxic effects. In a pilot study different doses (10, 100 and 400 mg/kg) of clomipramine hydrochloride were tested and it was found that 100 and 400 mg/kg in mini-pigs gave similar sedative effects and tachycardia as in man.

In a final study the doses were selected based on the pilot study and included two groups of mini-pigs, one dosed with clomipramine hydrochloride and the other with an equivalent dose of the clomipramine carrageenan complex. Administration of high doses of clomipramine carragenate generated lower plasma concentration of clomipramine than administration of the same dose of a conventional clomipramine hydrochloride preparation. There was a considerable difference in the toxical signs as shown below:

|  | Dose level | |
| --- | --- | --- |
|  | 100 mg/kg | 400 mg/kg |
| Clomipramine carragenate | No clinical signs considered to be related to the test article | |
| Clomipramine hydrochloride capsules | Sedative effect Weakness | Sedative effect Tachycardia |

Together with the in-vitro experiments, the results shows that the present invention should have a large potential in reducing toxic effects and lethality at overdosage of tricyclic antidepressants and other psychotropic agents.

EXAMPLE 1

15 g Nortriptyline hydrochloride was dissolved in 2000 ml distilled water. 15 g carrageenan (Aubygum×2) was added during stirring at room temperature. The slurry was stirred for 30 minutes and thereafter filtered through a cellulose filter.

The filter cake was dispersed in 1000 ml of distilled water and the slurry was filtered as before. The humid filter cake was allowed to dry during the night at 30°–50° C.

EXAMPLE 2

5 g Imipramine hydrochloride was dissolved in 100 ml distilled water. 5 g carrageenan (Aubygum×2) was added during stirring at room temperature. The slurry was stirred for 30 minutes and thereafter filtered through a cellulose filter.

The filter cake was dispersed in 100 ml distilled water and the slurry was fil-tered as before. The humid filter cake was allowed to dry during the night at 30° C.

EXAMPLE 3

10 g Amitriptylin hydrochloride was dissolved in 200 ml distilled water. 10 g carrageenan (Aubygum×2) was added during stirring at room temperature. The slurry was stirred for 30 minutes and thereafter filtered through a cellulose filter.

The filter cake was dispersed in 200 ml distilled water and the slurry was filtered as before. The humid filter cake was allowed to dry during the night at 30° C.

EXAMPLE 4

3 g Desipramine hydrochloride was dissolved in 150 ml distilled water 3 g carrageenan (Aubygum×2) was added during stirring at room temperature. The slurry was stirred for 30 minutes and thereafter filtered through a cellulose filter.

The filter cake was dispersed in 200 ml distilled water and the slurry was filtered as before. The humid filter cake was allowed to dry during the night at 30° C.

EXAMPLE 5

25 g Clomipramine hydrochloride was dissolved in 500 ml distilled water. 24 g carrageenan (Aubygum×2) was added during stirring at room temperature. The slurry was stirred for 60 minutes and thereafter filtered through a cellulose filter.

The filter cake was dispersed in 500 ml distilled water and the slurry was filtered as before. The humid filter cake was allowed to dry at 60°–65° C. for 16 hours.

EXAMPLE 6

20 mg Clomipramine carrageenate was filled into gelatin capsules together with various amounts of crystalline sodium chloride. The capsules were shaken with 50 ml 0.15M sodium chloride solution at 37° C. for 5 hours and subsequently analysed for the amount of released clomipramine (table 7).

EXAMPLE 7

10 g Amitriptylin hydrochloride was dissolved in 200 g distilled water. 22.1 g AG 50W-X4 was added during stirring at room temperature. The slurry was stirred for 45 minutes and thereafter filtered through a cellulose filter.

The filter cake was dispersed in 200 ml distilled water and the slurry was filtered as before. This procedure was repeated once. The humid filter cake was allowed to dry during the night at 60° C.

EXAMPLE 8

10 g Clomipramine hydrochloride was dissolved in 0.200 g distilled water 0.5 g Dextran sulphate was added during stirring at room temperature. The slurry was stirred for 45 minutes and thereafter filtered through a cellulose filter.

The filter cake was dispersed in 200 ml distilled water and the slurry was filtered as before. This procedure was repeated once. The humid filter cake was allowed to dry during the night at 60°C.

EXAMPLE 9

Preparation of Capsules

The dried material according to example 1–5 is milled through a suitable screen e.g with 1.5 mm orifices and filled into gelatin capsules to a suitable dose.

EXAMPLE 10

Preparation of Tablets

| Clomipramine tablets, 25 mg | |
| --- | --- |
| Clomipramine carragenate, milled | approx 50 mg |
| Microcrystalline cellulose | 50 mg |
| Crospovidon | 20 mg |
| Magnesium stearate | 4 mg |
| Colloidal anhydrous silica | 2 mg |

The ingredients are mixed and compressed to tablets.

EXAMPLE 11

Preparation of Suspensions

| 100 g of the suspension contans: | |
| --- | --- |
| Keltrol T | 0.4 g |
| Clomipramine complex | 1.0 g |
| Methyl parahydroxybenzoate | 0.1 g |

-continued

| 100 g of the suspension contans: | |
|---|---|
| Propyl parahydroxybenzoate | 0.02 g |
| Water, distilled | ad 100 ml |

Methyl parahydroxybenzoate and propyl parahydroxybenzoate are dissolved in distilled water. Keltrol-T is slowly added and dispersed in the solution. Finally the ion exchange complex is added while stirring.

TABLE 1

Data from the Swedish market obtained from SWEDIS, a computer based system in which all side effects reported to the authorities are registered.

| Substance | Number of deaths | Number of deaths probably associated with the drug | First reported side effect |
|---|---|---|---|
| Clomipramine | 5 | 2 | 1973 |
| Lofeptamine | 3 | 3 | 1980 |
| Maprotiline | 4 | 2 | 1977 |
| Amitriptyline | 2 | 2 | 1967 |
| Imipramine | 2 | 1 | 1965 |
| Moklobemide | 2 | — | 1990 |
| Trimipramine | 1 | 1 | 1965 |
| Mianserin | 1 | — | 1990 |
| Fludiazepam | 2 | 1 | 1981 |

TABLE 2

Dissolution of clomipramine from 40 mg clomipramine carrageenan complex in 1000 ml 0.1 M hydrochloric acid.

| Dissolution time (min) | 10 | 20 | 30 |
|---|---|---|---|
| % dissolution | 48 | 66 | 105 |

TABLE 3

Gastrointestinal secretions

| | Volyme/24 h | Electrolyte content, meqv/L | | | |
|---|---|---|---|---|---|
| | (ml) | Na | K | Cl | $HCO_3$ |
| Saliva | 500–1500 | 9–35 | 20–25 | 10–35 | 0–16 |
| Gastric juice | 1200–2500 | 35–60 | 9–20 | 84–150 | 0–7 |
| Bile | 500–600 | 140–149 | 5–10 | 100 | 30–40 |
| Pancreatic juice | 700–1200 | 140 | 5–10 | 75–77 | 75–100 |
| Intestinal secretes | 2000–3000 | 110–120 | 5–10 | 105 | 25 |
| Total | 5000–8000 | | | | |

Adapted from "Vätskebalans", Lars Thoren, 1960

TABLE 4

Amount extracted when 100 mg carrageenan complex was equilibrated with 0.15 M aqueous NaCl-solution for 5 hours.

| Volyme 0.15 M NaCl (l) | Desipramine | Extracted amount (%) Imipramine | Clomioramine |
|---|---|---|---|
| 0.05 | 42 | 43 | 17 |
| 0.15 | 93 | 97 | 45 |
| 0.25 | 98 | 99 | 63 |
| 0.32 | 98 | 101 | 74 |
| 0.49 | | | 102 |

TABLE 5

Amount clomipramine extracted from 100 mg clomipramine carrageenan complex equilibrated for 5 hours with 150 ml aqueous NaCl-solutions of different ionic strengths.

| Ionic strength (M) | 0.04 | 0.08 | 0.15 | 0.30 | 9.45 | 0.60 | 0.75 | 1.20 |
|---|---|---|---|---|---|---|---|---|
| Extracted amount (%) | 18 | 28 | 43 | 54 | 63 | 65 | 67 | 6 |

TABLE 6

Amount clomipramine, calculated as base, extracted from various amounts of clomipramine carrageenan complex after 5 hours equlibration with 1000 ml 0.15 M hydrochloric acid.

| Amount complex bound drug added (mg) | 106 | 196 | 330 |
|---|---|---|---|
| Amount extracted drug (mg) | 94 | 119 | 136 |

TABLE 7

Amount clomipramine extracted from various amounts of clomipramine carrageenan complex by 1000 ml of a solution of 0.15 M sodium chloride in water.

| Amount complex bound drug added (mg) | 109 | 149 | 201 | 331 | 1000 |
|---|---|---|---|---|---|
| Amount extracted drug (mg) | 105 | 112 | 124 | 144 | 158 |

TABLE 8

Amount amitryptiline extracted from a complex with AG 50W-X4 cation exchange resin by 1000 ml 0.15 M hydrochloric acid.

| Amount complex bound drug added (mg) | 31 | 64 | 149 | 315 | 612 | 955 | 1409 |
|---|---|---|---|---|---|---|---|
| Amount extracted (mg) | 14 | 25 | 37 | 50 | 56 | 64 | 60 |

TABLE 9

Amount clomipramine extracted from a complex with dextran sulphate by 1000 ml 0.15 M hydrochloric acid.

| Amount complex bound drug added (mg) | 12 | 23 | 53 | 118 | 514 | 760 | 1147 | 1568 |
|---|---|---|---|---|---|---|---|---|
| Amount extracted drug (mg) | 12 | 17 | 33 | 52 | 192 | 247 | 309 | 346 |

TABLE 10

Amount clomipramine extracted from clomipramine carrageenan complex after addition of sodium ions to the final preparation. For details about the procedure, see example 6.

| Amount of NaCl added (mg) | 214 | 442 | 661 | 867 |
|---|---|---|---|---|
| Amount extracted drug (%) | 69 | 74 | 89 | 94 |

TABLE 11

Extraction of Clomipramine from a carrageenan complex mixed with equal amounts of a competing cation-carrageenan complex. Extraction medium: 1000 ml 0.15 M hydrochloric acid.

| Amount complex bound Clomipramine added (mg) | 34 | 62 | 129 | 313 | 518 | 650 |
|---|---|---|---|---|---|---|
| Amount extracted Clomipramine (mg) | 34 | 59 | 86 | 94 | 92 | 93 |

We claim:

1. An oral pharmaceutical composition providing a preventing effect against toxic overdoses of a psychotropic drug comprising a mixture of:
   a) a psychotropic drug having a ionizable amino group complexed to a carrageenan cation exchanger:
   b) an additional substance capable of generating cations which affects the amount of available ions for ion exchange and thereby is capable of ceasing the psychotropic drug release rate when said psychotropic drug is administered in an amount exceeding normal doses, wherein said additional substance is selected from the group consisting of:
      i) sodium chloride which generates a sodium ion with higher or similar affinity to the carrageenan cation exchanger compared to said psychotropic drug, and
      ii) an ionizable amine capable of acting as a counter ion in a competing complex with a carrageenan cation exchanger, wherein said amine has less or similar affinity to said carrageenan cation exchanger compared to said psychotropic drug.

2. A composition according to claim 1, wherein said counter ions are biologically inert amines.

3. A composition according to claim 2, wherein said psychotropic drug is a tricyclic or tetracyclic antidepressant having an ionizable amino group.

4. A composition according to claim 1, wherein said psychotropic drug is a tricyclic or tetracyclic antidepressant having an ionizable amino group.

5. A method of preventing toxic side-effects after orally overdosing a psychotropic drug having an ionizable amino group which is complexed to a carrageenan cation exchanger which comprises adding to said drug complexed to said carrageenan cation exchanger an additional substance capable of affecting the amount of ions available for ion exchange of said drug, wherein said additional substance is selected from the group consisting of:
   a) sodium chloride which generates a sodium ion with higher or similar affinity to said carrageenan cation exchanger compared to said psychotropic drug, and
   b) an ionizable amine capable of acting as a counter ion in a competing complex with a carrageenan cation exchanger, wherein said counter ion has less or similar affinity to said carrageenan cation exchanger compared to said psychotropic drug.

6. A method according to claim 5, wherein said psychotropic drug is a tricyclic or tetracyclic antidepressant.

7. A method according to claim 5, wherein the counter ion is biologically inert amine.

8. A method according to claim 6, wherein the counter ion is biologically inert amine.

* * * * *